United States Patent [19]
Chien

[11] Patent Number: 5,404,745
[45] Date of Patent: * Apr. 11, 1995

[54] METHOD AND APPARATUS FOR DETERMINING STEAM QUALITY FROM STEAM VELOCITY MEASUREMENT

[75] Inventor: Sze-Foo Chien, Houston, Tex.

[73] Assignee: Texaco Inc., White Plains, N.Y.

[*] Notice: The portion of the term of this patent subsequent to Mar. 3, 2009 has been disclaimed.

[21] Appl. No.: 963,217

[22] Filed: Oct. 19, 1992

Related U.S. Application Data

[63] Continuation-in-part of Ser. No. 597,646, Oct. 15, 1990, abandoned.

[51] Int. Cl.$^6$ ............................................. G01N 7/00
[52] U.S. Cl. ................................... 73/29.01; 73/861.04
[58] Field of Search ............... 73/29.01, 29.03, 861.04

[56] References Cited

U.S. PATENT DOCUMENTS

| 4,836,032 | 6/1989 | Redus et al. | 73/29.01 X |
| 5,031,465 | 7/1991 | Redus | 73/29.03 X |
| 5,031,466 | 7/1991 | Redus | 73/29.03 X |
| 5,035,146 | 7/1991 | Chien | 73/29.01 X |
| 5,092,159 | 3/1992 | Chien | 73/29.03 |

Primary Examiner—Hezron E. Williams
Assistant Examiner—Michael Brock
Attorney, Agent, or Firm—Kenneth R. Priem; James L. Bailey

[57] ABSTRACT

A method and apparatus for determining and monitoring the quality of steam by measuring the critical velocity of the steam flowing through a nozzle.

2 Claims, 2 Drawing Sheets

METHOD AND APPARATUS FOR DETERMINING STEAM QUALITY FROM STEAM VELOCITY MEASUREMENT

CROSS REFERENCE TO RELATED PATENT APPLICATION

This is a Continuation-in-Part of my patent applications Ser. NO. 07/597,646, filed Oct. 15, 1990, now abandoned.

BACKGROUND OF THE INVENTION

1. The Field of the Invention

The present invention relates to a method an apparatus to determine the quality of steam by measuring the velocity of steam flowing through the throat of a nozzle under critical flow conditions.

2. The Prior Art

Steam flooding has become an accepted practice for recovery of petroleum products from marginal fields or reservoirs that require a degree of stimulation to produce a satisfactory flow of crude petroleum. There is a need for a simple method and apparatus to determine the quality of steam at the wellhead of an injection well and at any location of the steam distribution network. The wellhead measurement, if simplified, would be particularly useful in determining the amount of heat which is applied to the underground reservoir by the injected steam.

The measurement or monitoring of steam quality is important since the steam's quality, and thereby its ability to heat up the reservoir or formation, affects the resulting production operations. Further, the quality of the steam which can be most economically injected into a particular substrate or reservoir is contingent on a number of circumstances. These include the age of the reservoir and the anticipated prospects for extracting commercially justified amounts of hydrocarbon products therefrom.

In brief, it is desirable that the quality of steam which is injected into each injection well be altered or adjusted to a level of quality that best conforms to the condition of the formation being produced by that well. Clearly the quality of the steam must be known before any alteration or adjustment can be made.

It is known that in order to be particularly effective in this type of stimulation operation, the flow of injected steam must be monitored by use of metering means positioned in the steam-carrying line adjacent the wellhead. It can be appreciated that steam will normally leave the steam generator or source at a known quality, pressure and mass flow rate. As the pressurized steam flow progresses towards an injection well, however, the quality will usually be substantially decreased. A decrease in the quality can be based on such factors as the distance between the well and the source and the effectiveness of pipe insulation. It will further depend on the pipe layout including number and orientation of fittings through which the steam has to travel prior to reaching the injection port or well because of phase separation that can occur in these fittings.

U.S. Pat. No. 4,836,032 discloses the use of an orifice plate in series with a critical flow choke to provide a method of measurement for both steam quality and mass flow rate. Either the orifice plate or the choke alone can be used to measure steam quality and mass flow rate. The invention described in this patent application is to measure only the steam quality.

U.S. Pat. No. 4,324,143 discloses a flowmeter to measure the flow rate of air at low pressure and low flow rate for automotive internal combustion engines. Although this invention involves a venturi it is primarily focused on sets of swirling vanes of specific design aimed to obtain an improved metering of the flow rate for air at low pressure and low velocity condition. The present invention is distinguished from this prior art in that it is used to determine the quality of steam by measuring its critical or sonic velocity at the throat to a nozzle.

U.S. Pat. No. 2,060,848 discloses an improved air velocity meter for measuring air or gas at very low velocities. One way to use this invention is to connect the meter to a probe which consists of two tubes that can be inserted through a hole on the side of the main air or gas duct. However, this invention is primarily concerned with the specific features of the air velocity meter.

It should be emphasized that the present invention is concerned with the determination of the steam quality by measuring the critical velocity of the steam at the throat of a nozzle. The usefulness of the present invention is for steam which is usually at a high pressures ranging from several hundreds to thousands psia. A unique feature of the present invention is based on the fact that the critical velocity of steam is a function of steam quality. The critical velocity of steam increases as the steam quality is increased. The magnitude of velocity is the highest velocity the steam can achieved under the prescribed condition. It can be from several hundred to more than one thousand feet per second. Clearly, the objective of the measurement, the type of fluid, the range of pressure and velocity are distinctly differed from those described in the above mentioned patents.

SUMMARY OF THE INVENTION

The present invention claims a method and apparatus to determine the quality of steam by measuring the velocity of the steam at the throat of a nozzle where the steam is flowing under critical flow conditions. The nozzle can be either a part of the steam flow system or a part of a quality sampling probe. The quality is either calculated from a correlation or an calibration curve expressing the quality as function of the critical velocity.

BRIEF DESCRIPTION OF THE DRAWINGS

The present invention will now be described by way of example with reference to the accompanying drawings, in which.

DETAILED DESCRIPTION OF THE PREFERRED EMBODIMENT

Figure 1:
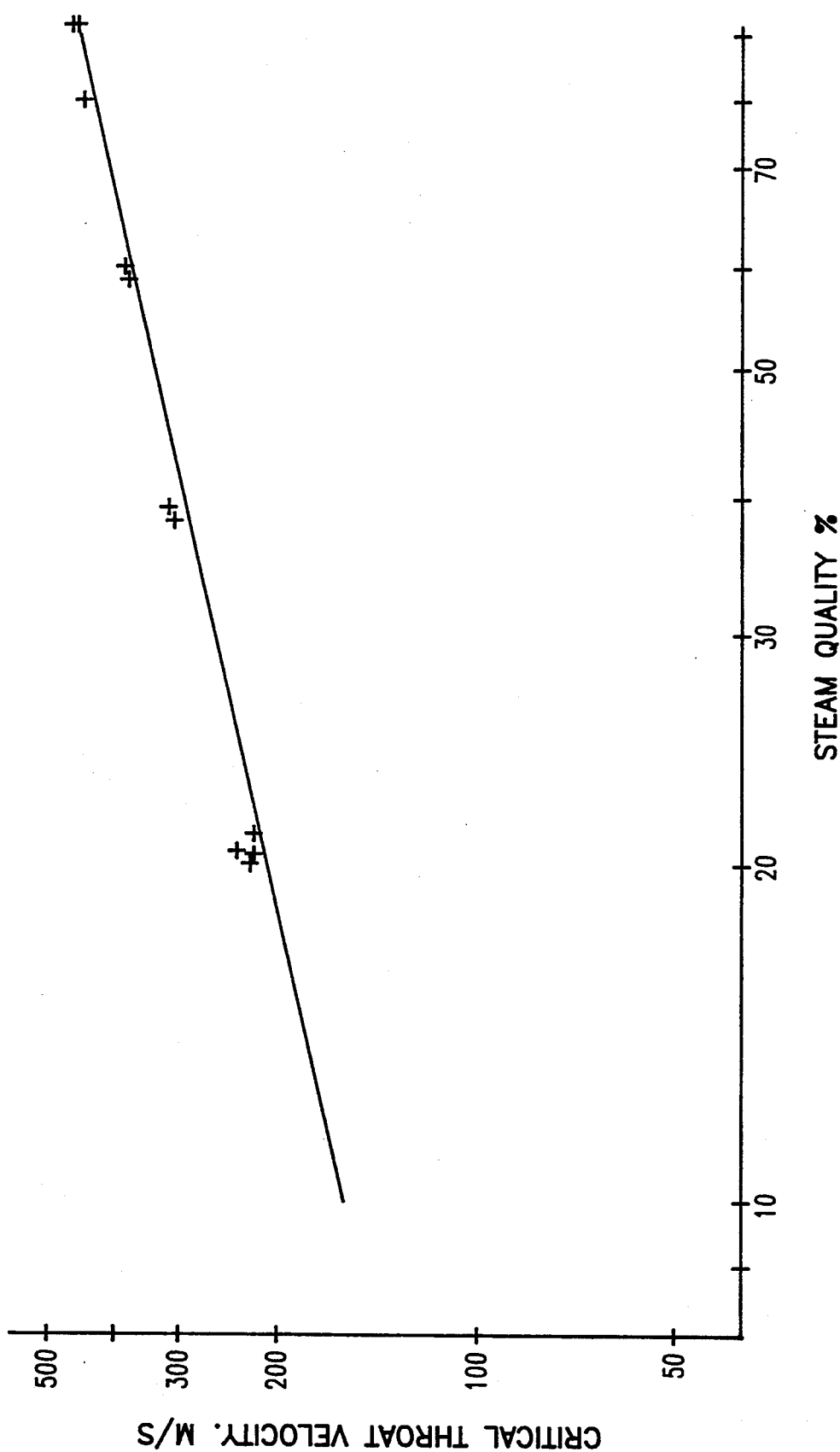
FIG. 1 is a graph plotting the relationship between the critical velocity of the steam and the quality of steam.

Analytical study of the critical flow of steam established that the critical velocity of steam is a simple function of the steam quality for a wide range of steam pressures. FIG. 1 shows the relationship between the critical velocity and the steam quality. The analytical result is for steam at pressure from 380 to 1040 psia and the experimental data are for steam at pressure in the 414 to 814 psia range. Note that the pressure does not effect the critical velocity. The experimental data are those for critical flow through a nozzle with 24/64 in. throat diameter and 8° nozzle angle. These critical velocities are calculated from the flow rate, throat diameter and the throat pressure. The graph data strongly support the basic concept of using critical velocity to determine steam quality. In the present invention, the steam flows through a nozzle under critical flow conditions. The velocity at the throat of a nozzle can be determined by appropriate velocity transducers (such as a Pitot static tube type transducer) and its signal can be readily processed to convert to steam quality. For FIG. 1, a correlation can be developed to express the steam quality as a function of the critical throat velocity:

$$\text{Steam Quality in Percent} = \left(\frac{\text{velocity, ft/sec}}{186.64}\right)^{2.188}$$

where X is steam quality in percent.

Figure 2:
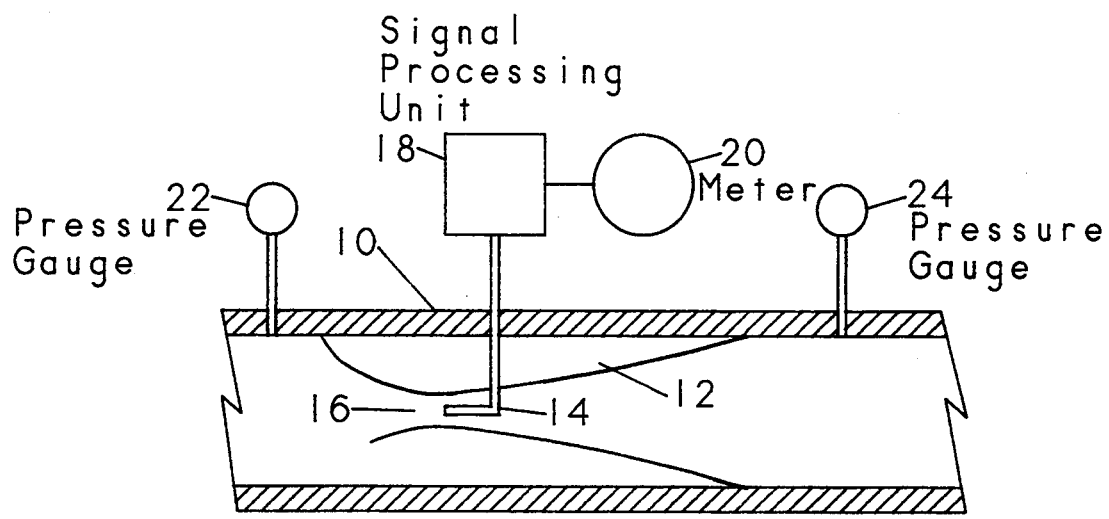
FIG. 2 is a diagrammatic section through a first embodiment of an apparatus suitable for use with the present invention where the nozzle is a part of the flow system.
Figure 3:
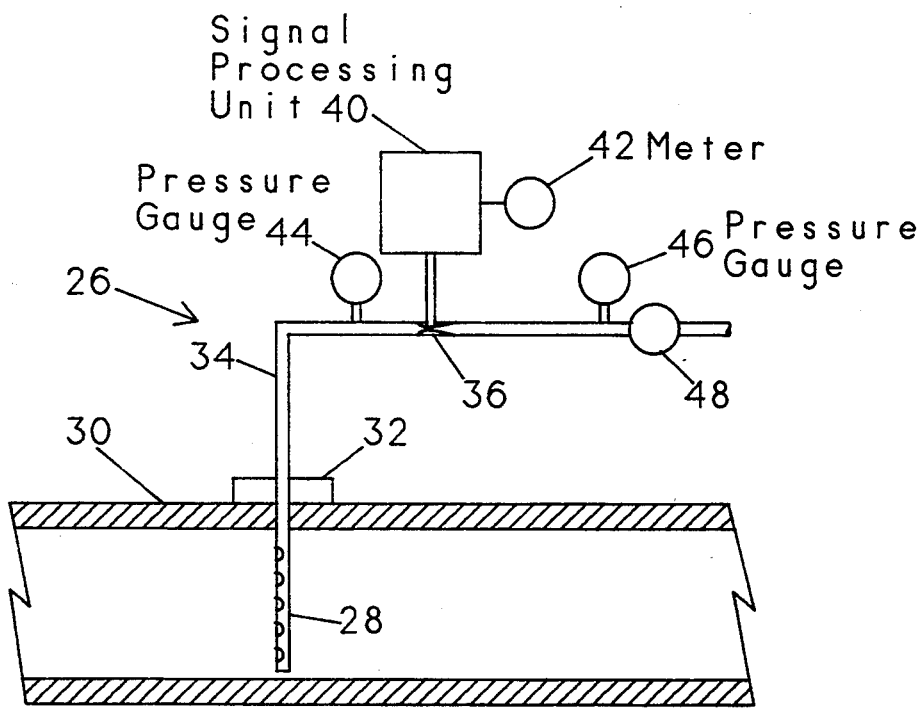
FIG. 3 is a diagrammatic section through a second embodiment of an apparatus suitable for use with the present invention where the nozzle is a part of a quality sampling probe.

The nozzle required by the present invention can be either as a part of the flow line (FIG. 2) or part of a portable unit (FIG. 3). FIG. 2 shows a steam flow line 10 having nozzle 12 fixedly mounted therein. A velocity transducer 14 is positioned at the throat 16 of the nozzle 12. The signal from the velocity transducer 14 is sent to and processed by signal processing unit 18. The signal process unit 18 calculates the steam quality according to the equation shown above or according to an experimentally determined relationship between the critical velocity and the steam quality. The result of calculation is then fed to an appropriate meter 20, where the information of steam quality can be directly displayed or transmitted to a remote location (not shown). An upstream pressure gauge 22 and a downstream pressure gauge 24 are situated at the upstream and downstream of the nozzle 12 to measure pressure. To assure critical flow through the nozzle 12, the downstream pressure should be equal to or less than half of the upstream pressure. This implies that the throat diameter of the nozzle should be sized accordingly to achieve this critical flow condition.

FIG. 3 shows a portable unit 26 connected to a sampling probe 28. The sampling probe 28 is suitable for tapping into larger diameter steam lines 30 via a known tap 32. It is particularly useful for instances when one does not want to have a critical flow nozzle permanently fixed in the flow line. The sampled fluid is led from the probe 28 through tubing 34 containing a small nozzle 36, where the flow is at critical flow conditions. The velocity at the throat of the nozzle 36 is measured by a velocity transducer 38. The output of the velocity transducer 38 is then processed by signal processing unit 40 to determine the steam quality according to the correlation shown above or according to an experimentally determined relationship between the critical velocity and the steam quality, as one similar to FIG. 1. The result of quality can be displayed on the meter 42 or transmitted to a remote location. Pressure gauges 44 and 46 are situated upstream and downstream of the nozzle, respectively, to measure pressure upstream and downstream of the nozzle. An adjustable valve 48 is situated at the discharge end of the probe. To assure critical flow through the nozzle 36, the valve 48 should be adjusted so that the pressure reading at the downstream gauge 46 is equal to or less than that at the upstream gauge 44.

The present invention may be subject to many modifications and changes without departing from the spirit or essential characteristics thereof. The present embodiments should therefore be considered in all respects as being illustrative and not restrictive of the scope of the present invention as defined by the appended claims.

I claim:

1. A device for determining steam quality of wet steam at critical flow in a line, said device comprising:
    a nozzle positioned in said line and having a throat substantially coaxial therewith;
    a velocity measuring means positioned in the throat of said nozzle whereby the velocity of said steam through the nozzle is measured;
    first pressure gauge means in said flow line upstream of the nozzle;
    second pressure gauge means in said flow line downstream of the nozzle;
    signal process means connected to receive an output from said velocity measuring means and to calculate the quality of the steam from the value of the measured critical velocity; and
    meter means connected to said signal process means to display the calculated quality.

2. A device for determining steam quality of wet steam at critical flow in a steam line, said device comprising:
    sampling probe means for selective insertion into said steam line;
    conduit means connected to said sampling probe and containing a nozzle through which the steam sample flows at critical flow condition; and
    velocity transducer means at the throat of said nozzle whereby the velocity of the sampled steam at critical flow is measured;
    first pressure gauge means connected to said conduit means upstream of the nozzle;
    second pressure gauge means connected to said conduit means downstream of the nozzle;
    signal processing means connected to said velocity transducer means to calculate steam quality from the measured critical velocity; and
    meter means connected to said signal processing means to display the calculated steam quality.

* * * * *